United States Patent [19]  [11]  4,334,540
Preti et al.  [45]  Jun. 15, 1982

[54] METHOD OF DIAGNOSING PERIODONTAL DISEASE THROUGH THE DETECTION OF PYRIDINE COMPOUNDS

[75] Inventors: George Preti, Philadelphia; James G. Kostelc, Glenside; Philip R. Zelson, Drexel Hill, all of Pa.

[73] Assignee: Monell Chemical Senses Center, Philadelphia, Pa.

[21] Appl. No.: 35,018

[22] Filed: May 1, 1979

[51] Int. Cl.³ .......................... A61B 5/00; G01N 1/00; G01N 33/48
[52] U.S. Cl. .................................... 128/630; 128/717; 128/719; 424/9
[58] Field of Search ..................... 424/9; 128/630, 717, 128/719

[56] References Cited

U.S. PATENT DOCUMENTS 3,986,494 10/1976 Preti et al. .......................... 128/2 R
4,010,738 3/1977 Preti et al. .......................... 128/2 R
4,119,089 10/1978 Preti et al. .......................... 128/2 R

OTHER PUBLICATIONS

Tonzetich, Arch. Oral Biol., vol. 9, 1964, pp. 39–45.
Lindhe, J. Periodont. Res., vol. 2, 1967, pp. 194–198.
Zelson et al., IADR Abstracts, 1978, J. Dent. Res., vol. 57, Jan. 1978, Ab. No. 679.
Dreizen, Oral Surg., vol. 9, 1956, pp. 278–283.
Main, Brit. J. Dermat., vol. 79, 1967, pp. 20–30.
Teranishi, Analytical Chem., vol. 44, 1972, pp. 18–20.
Chen, J. Lab. & Clin. Med., vol. 75, 1970, pp. 622–627, and 628–635.
Charalambous (Ed), Analysis of Foods & Beverages, Acd. Press, N. Y., 1978, pp. 283–357.
Kostelc et al., IADR Abstrats, 1979, J. Dent. Res., vol. 58, Jan. 1979, Ab. No. 325.
Dolby (Ed), Oral Mucosa in Health & Dis., Blackwell Sci. Pub. Oxford, pp. 113–116.
Afonsky, Saliva & Its Relation to Oral Health, U. of Ala. Press, 1961, pp. 97–104.
Brunneman, Chem. Abs., vol. 89, 1978, Ab. No. 89:194115x.
Golub, J. Periodont. Res., vol. 6, 1971, pp. 243–251.
Loe, Acta Odont. Scand., vol. 21, 1963, pp. 533–549.
Rizzo, Periodontics, vol. 5, No. 5, 1967, pp. 233–236.
Lindhe, J. Perodont. Res., vol. 3, 1968, pp. 12–20.
Miles, Brit. Dent. J., vol. 105, No. 7, 1958, pp. 235–248.
McNamara, Oral Surg., vol. 34, Jul. 1972, pp. 41–48.
Loe, J. of Periodont., vol. 36, 1965, pp. 37/209–45/217.
Grant, WHM, Toxicology of the Eye, C. C. Thomas, Pub., 1962.
Lorber, Am. Rev. Respiratory Dis., vol. 112, 1975, pp. 875–876.
Berg, J. Dent. Res., vol. 26, 1947, pp. 67–71.
Law, J. Dent. Res., vol. 22, 1943, pp. 373–379.
Ramfjord, J. Periodont., vol. 30, 1959, pp. 51–59.
Tonzetich, J. Int. Med. Res., vol. 6, 1978, pp. 245–254.
Tonzetich, Archs. Oral Biol., vol. 16, 1971, pp. 587–597.
Thompson, Analytical Chem., vol. 47, Jul. 1975, pp. 1313–1321.
Tonzetich, J. Periodont., vol. 48, 1977, pp. 13–20.
Rao, J. Dent. Res., vol. 57(A), 1978, p. 244, Ab. No. 680.
Labows, J. of Chromat. Biomed. Applications, vol. 163, 179, pp. 294–299.
Tonzetich, Int. Dent. J., vol. 28, 1978, pp. 309–319.
Doty, R., "Procedure for Combining Menstrual Cycle Date", Journal of Clinical Endocrinology & Metabolism, vol. 48, No. 6, Jun. 1979, pp. 912–918.
Watson, Analytical Chem., vol. 37, Jun. 1965, pp. 844–851.
Moss, C. W. and S. B. Dees, "Cellular fatty acids and metabolic products of Pseudomonas species obtained from clinical specimens"; Journal of Clinical Microbiology 4: 492–502 (1976).
Wade, T. J. and R. J. Mandel, 1974, "New gas Chromatographic characterization procedure": preliminary studies on some Pseudomonas species Applied Microbiology 27: 303–311, Feb. 1974.
Tonzetich, Oral Surg., vol. 42, 1976, pp. 172–181.
Charles D. Cox and J. Parker, "Use of 2-aminoacetophenone production in identification of *Pseudomonas aeruginosa*", Journal of Clinical Microbiology, Apr. 1979, 9: 479–484.
Hayward et al., "Development of specific tests for rapid detection of *E. coli* and species of Proteus in urine", Journal of Clinical Microbiology, Sep. 1977, 6: 195–201.

Van den Dool, J. of Chromat., vol. 11, 1963, pp. 463–471.

Miller et al., "Volatile Compounds Produced in Sterile Fish (Sebastes malanops) by Pseudomonas putrefaciens, Pseudomonas fluorescens, and an Achromobacter Species", Applied Microbiology, 26: 18–21, Jul. 1973.

Lee et al., "High resolution gas chromatographic profiles of volatile organic compounds produced by microorganisms at refrigerated temperatures", Applied and Environmental Microbiology No. 1 37: 85–90, Jan. 1979.

Tonzetich, Archs. Oral Biol., vol. 23, 1978, pp. 875–880.

Brunn et al., "Epidemiology of *Pseudomanas aeruginosa* infections: determination by Pyocin typing", Journal of Microbiology, 3: 264–271 (1976).

Laraya-Cuasay et al., "Pseudomonas carrier rates of patients with cystic fibrosis and of members of their families", Journal of Pediatrics, 89: 23–26 (1980).

Tonzetich, Archs. Oral. Biol., vol. 14, 1969, pp. 815–827.

Mitruka, "Gas chromatography application in microbiology and medicine", (1979), John Wiley & Sons, New York, Chapter 13, 352–374.

Brooks et al., "Further studies on the differentiation of *Clostridium sordelli* from *Clostridium bifermentans* by gas chromatography", Canadian Journal of Microbiology 16: 1071–1078 (1970).

Holzer, J. of Chromat., vol. 142, 1977, pp. 755–764.

"Analysis by gas chromatography of fatty acids found in whole cultural extracts of Neisseria species", Can. J. Microbiol. 17: 531–541 (1970).

Brooks et al., "Analysis by gas chromatography of hydroxy acids produced by several species of Neisseria", Canadian Journal of Microbiology 18: 157–168 (1972).

Golub, Oral Sci. Rev., vol. 8, pp. 49–61.

Kostelc et al., "Salivary volatiles as indicators of periodontitis", J. Periodont. Res. 18: 185–192 (1980).

Matsumota et al., "Identification of volatile compounds in human urine", J. Chromatogr. 85: 31–34 (1973).

Rooth, The Lancet, II, 19 Nov. 1966, pp. 1102–1105.

Zlatkis et al., "Concentration and analysis of volatile urinary metabolites", J. Chromatogr. Sci. 11: 299–302 (1973).

Reiner et al., "Botulism: A pyrolysis-gas-liquid chromatographic study", J. Chromatogr. Sci. 16: 623–629 (1978).

Russell, J. Dent. Res., vol. 35, 1956, pp. 350–359.

Bohannon et al., "Quantitative methods for the gas chromatographic characterization of acidic fermentation by-products of anaerobic bacteria", J. of Chromatogr. Sci. 16: 28–35 (1978).

Larsson et al., "Analysis of Amines and other bacterial products by head-space gas chromatography", Acta Path. Microbiol. Scand. Section B 86: 207–213 (1978).

Simenhoff, N. E. J. Med., vol. 297, 1977, pp. 132–135.

Hayward et al., "Methylmercaptan and DMDS production from methionine by Proteus Species Detected by Head-Space Gas-Liquid Chromatography", J. of Clin. Microbiol. 6: 187–194 (1977).

Labows et al., "Characteristic Gamma-Lactone odor production of the genus Pityrosporum", Appl. and Environ. Micro. 38: 412–415 (1979).

Sicher(ed) Orban's Oral Histology & Embryology, Mosby, St. Louis, 1972, pp. 269–271.

Morgan, "The chemistry of some microbially-induced flavor defects in milk and dairy foods", Biotech. Bioeng. 18: 953–965 (1976).

Liebich et al., "Volatile substances in blood serum: profile analysis and quantitative determination", J. Chromatogr. 142: 505–516 (1977).

Holm-Pedersen, J. Periodont. Res., vol. 2, 1967, pp. 13–20.

Withycombe et al., "Isolation and identification of volatile components from wild rice grain", J. of Agricultural Food Chemistry, vol. 6, pp. 816–821, (1978).

Budzikiewicz et al., "Mass spectrometry of organic compounds", p. 155, Holden-Day, Inc., San Francisco (1967).

Iusem, Oral Surg., vol. 3, 1950, pp. 1516–1520.

Dwivedi et al., "Carbonyl production from lipolyzed milk fat by the continuous mycelial culture of *Penicillium roqueforti*", J. Food Science, 39: 83–137 (1974).

Burger et al., "Ketones from the pedal gland of the bontebok", Z. Naturforsch C: Bioscience, 316: (1–2): 21–28 (1976).

Hafez(ed), The Human Vagina, North-Holland Pub., N. Y., 1978, pp. 151–166.

Albone et al., "Bacteria as a source of chemical signals in Mammals", reprinted pp. 35–43 in D. MullerSchwarze & M. M. Mozell, Editors, Chemicals Signals in Vertebrates, Plenum Press, N.Y. (1977).

Ikeshoji, "Bacterial production of the ovipositional attractants for mosquitos on fatty acid substrates", App. Ent. Zool. 10: 239-242, (1975).

Jellum, Analytical Chem., vol. 45, 1973, pp. 1099-1106.

Labows et al., "Headspace Analysis of Volatile Metabolites of *Pseudamonas aerugino* and Related Species by Gas Chromatography-Mass Spectrometry", J. Clin. Microbiol., vol. 12, Oct. 1980, pp. 521-526.

Gorbach, S. L., J. W. Mayhew, J. G. Bartlett, II. Thadepalli, and A. B. Onderdonk. Rapid Diagnosis of anaerobic infections by direct gas-liquid chromatography of clinical specimens, J. Clin. Invest. 57: 478-484, (1976).

Hutterer, Clin. Chem., vol. 17, 1971, pp. 789-794.

Berg and Fosdick, J. Dental Res., vol. 25, pp. 73-81 (1946).

Tonzetich, Arch. Oral Biology, 4: 587-597, (1971).

Zlatkis, Chromatographia, vol. 6, 1973, pp. 67-70.

Berg et al., J. Dental Res., vol. 26, pp. 67-71 (1947).

Jamison, J. 1960 Prevalence and Severity of Periodontal Disease on a Sample Population, Thesis, University of Michigan, School of Public Health, Ann Arbor.

Dubowski, Clin. Chem., vol. 20, No. 8, 1974, pp. 966-972.

Tonzetich, J. Oral Malodour: An Indicator of Health Status and Oral Cleanliness. Int. Dent. J., 28: 309-319 (1978).

Silness, Acta Odont. Scand., vol. 22, 1964, pp. 121-135.

DePaola, Nutrition Today, vol. 12, 1977, pp. 6-11, 29-32.

Hardie, The Normal Microbial Flora of Man, Acd. Press, N. Y., 1974, pp. 47-61.

Spouge, The Dental Pract., vol. XIV, Apr. 1964, pp. 307-317.

*Primary Examiner*—Anna P. Fagelson
*Attorney, Agent, or Firm*—Woodcock, Washburn, Kurtz, Mackiewicz & Norris

[57]     ABSTRACT

A novel method of diagnosing periodontal disease is disclosed wherein telltale pyridine and alkyl-pyridine compounds which are detected in the oral cavity are indicative of periodontal disease. An alternate embodiment method is disclosed wherein increased concentrations of certain other compounds are detected to confirm the presence of periodontal disease.

17 Claims, 3 Drawing Figures

METHOD OF DIAGNOSING PERIODONTAL DISEASE THROUGH THE DETECTION OF PYRIDINE COMPOUNDS

BACKGROUND OF THE INVENTION

Periodontal disease is a destructive inflammatory process which destroys the supporting structures of teeth. While this disease is relatively easy to identify in its advanced stages, early diagnosis of the disease has been a long-sought objective of research in this area, since such diagnosis would enable timely preventive measures to be taken. Periodontal disease is widespread, effecting a majority of people over 35 years of age, and is a major cause of tooth loss and destruction of supporting bone tissue.

Although the precise cause of inflammatory periodontal disease remains unclear, certain factors have been associated in the literature with its origin. These include local irritants, such as bacterial plaque, faulty restorations, and traumatic tooth contacts. Systematic factors, such as hormonal and nutritional status, also affect the course of the disease. Despite this variety of factors, it is widely accepted that the primary causative agent in periodontal disease is the bacterial plaque located in the gingival crevice (the space between the surface of the tooth and the gingiva). When plaque develops in this area, it constitutes one of the most dense concentrations of bacteria to which man is exposed. These and other factors are discussed in some detail in an article entitled "Diet and Oral Health", by Dominick P. DePaola, D.D.S., Ph.D. and Michael C. Alfano, D.M.D., Ph.D. appearing in "*Nutrition Today*", May/June 1977.

While considerable research has been conducted on individuals with periodontal disease, this research has heretofore failed to produce a reliable early diagnostic indicator for the existance of periodontal disease. For example, it has long been known that saliva from patients suffering from periodontal disease putrefies more rapidly than saliva from health oral cavities (Berg, M., Burrill, D.Y., and Fosdick, L.S. 1947, Chemical Studies In Periodontal Disease. IV. Putrefaction Rate As Index Of Periodontal Disease. J. Dent. Res. 26: 67–71; Law, D.B., Berg, M.S., and Fosdick, L.S. 1943. Chemical Studies In Periodontal Disease. J. Dent. Res. 22: 373–379). Of course, it has also been noted that other factors, such as monthly hormonal variations in female subjects, (as reported by Tonzetich, J., Preti, G., and Huggins, G.R. 1978, Changes In Concentrations Of Volatile Sulfur Compounds Of Mouth Air During The Menstrual Cycle. J. Int. Med. Res., 6: 245–254) may exert strong influences on saliva and mouth air samples, as may drug and medication use, dietary intake and normal dental hygienic procedures.

It is well documented that quantitative changes in the concentration of certain metabolites excreted in human body fluids, as well as in expired mouth air, can provide indications of a number of pathologic or physiologic events. For example, with respect to body fluids, see Jellum, et al, J. Anal. Chem. 45(7):1099–1106, 1973; Thompson and Markey, J. Anal. Chem. 47(8):1313–1321, 1976; Hutterer, Clin. Chem. 17(8):789–794, et al, 1971; Zlatkis, 789–794, et al, Chromatographia 6(2):67–70, 1973; Preti and Huggins, The Human Vagina, Chapter 10, (1978). For example, expired mouth air contains a complex mixture of organic compounds of both systemic and oral origin (Tonzetich, Arch Oral Biology, Volume 16, pages 587–597 1971; Dubowski, Clin. Chem. 20(8):966–972, 1974; Teranishi, et al, Anal. Chem. 44(1):18–20, 1972). Protocols have been devised for determining blood ethanol levels via its concentration in breath (Dubowski, Ibid., 1974). In addition to ethanol, other organic metabolites of systemic origin found in breath have been identified (Chen, et al, J. of Lab. and Clinical Medicine, Vol. 75, No. 4, pp. 622–627 and pp. 628–635, 1970 a, b; Dubowski, Ibid., 1974).

Saliva consists of secretions from the parotid, submandibular and sublingual glands and fluids from numerous minor glands distributed throughout the oral cavity. In addition, mixed saliva contains gingival exudate, leukocytes, exfoliated epithelial cells, microorganisms and food debris (Orban, Oral Histology and Embryology, pp. 269–271, 1972; MacFarlane and Mason, Oral Mucosa In Health, Blackwell Scientific Publications, pp. 113–116, 1975).

The nature and abundance of many of the inorganic and organic constituents found in saliva have been documented (Afonsky, University of Alabama Press, pp 97–104 1961; MacFarlane and Mason, Ibid., 1975). Although many of the investigations of the organic constituents of saliva have been aimed primarily at characterizing the nature of the large molecules present, some smaller (M.W.$\leq$450) organic molecules have been identified. These are listed in Table 1. Lipids present in skin sebum may also be present in saliva (Miles, British Dental Journal 104:235–248, 1958; MacFarlane and Mason, Ibid., 1975). The putrefactive action of microorganisms on proteinaceous substrates in saliva is the source of many volatiles found in mouth air (see below) (Spouge, The Dental Practitioner and Dental Record, Vol. XIV(8):307–317, 1964; Tonzetich and Kestenbaum, Arch.Oral Biol. 14:815–827, 1969; McNamara et al, Oral Surg. 34:41–48, 1972). The distribution of normal microflora in the various areas of the oral cavity has recently been reviewed (Hardie and Bowden, The Normal Microbial Flora of Man, pp. 47–61, 1974), and many of the microorganisms and indigenous to the saliva, tongue, dental plaque and gingival crevice are reported to produce volatiles (Berg and Fosdick, J. Dental Res., Vol. 26, pp. 67–71; J. Dental Res., Vol. 25, pp. 73–81, 1946; McNamara et al, Ibid., 1972).

A number of volatile compounds produced are primarily in the oral cavity. The volatile sulfur compounds, hydrogen sulfide ($H_2S$), methylmercaptan ($CH_3SH$) and dimethylsulfide ($(CH_3)_2S$), produced by metabolic processes within the oral cavity, have been extensively studied because they are responsible for oral malodor (Tonzetich and Kestenbaum, Ibid., 1969; Tonzetich, Arch. Oral Biol. 4:587–597, 1971). This malodor is manifested due to the production of volatile compounds through putrefaction by microorganisms (Berg and Fosdick, Ibid., 1946) on proteinaceous substrates, exfoliated epithelial cells, salivary corpuscles, food debris, saliva and blood. The proteins are degraded via proteolysis to peptides and amino acids which are further metabolized to the volatile sulfur compounds (VSC) (Tonzetich and Kestenbaum, Ibid., 1969). The VSC in mouth air are decreased by brushing and rinsing. All individuals produce them, but they are accentuated in tissue degenerative conditions such as gingivitis, periodontitis, and acute necrotizing ulcerative gingivitis (J. Periodont. 48:13–20, 1977).

In addition, general relationships between oral conditions favorable for VSC production and phases of the menstrual cycle have been demonstrated by several studies. Elevated levels of estrogens and progesterone appear to lower the threshold sensitivity of human periodontal tissues to inflammation (Loe, J. of Periodentology, V. 36(1):37/209–45/217, 1965; Loe and Sillness, Acta Odont. Scand. 21:533–549, 1963). The severity of tissue involvement is correlated with an increase in the volume of gingival fluid and is greatest near ovulation and least at menstruation (Lindhe and Attstrom, J. Periodont. Res. 2:194–198, 1967; Lindge et al, J. Periodont. Res. 3:12–20, 1968). The greatest fluctuations in the volume of gingival exudate due to hormonal influences occur in females with pre-existing chronic gingivitis (Holm-Pedersen and Loe, J. Perio. Res. 2:13–20, 1967). Other factors that lead to VSC production are increases in the number of desquamated epithelial cells during menstruation, during ovulation ((Iusem, Oral Med. 3:1516–1520, 1950; Main and Richie, Brit. J. Dermatology 79:20–30, 1967), in periodontitis (Dreizen et al, Oral Surgery, Oral Medicine and Oral Pathology 69:278–283, 1965), and during menstruation and ovulation due to elevated total bacterial counts.

A recent study at the Monell Chemical Senses Center employing high sensitivity GC has provided the first direct evidence that VSC may fluctuate during the menstrual cycle and correlate with changes in circulating sex steroid hormone levels (Tonzetich et al, J. Internat. Med. Res. 6:245–254, 1978). Consequently, in examining ovulating female patients for volatile mouth air constituents, the time of the menstrual cycle should be noted.

Saliva samples from patients with periodontal disease putrefy more rapidly than do those without this problem (Berg et al, J. Dental Res., Vol. 26, pp. 67–71, 1947; Law et al, J. Dental Res. 22:373–379, 1943). This may be due to the increase in number and type of microorganisms. Regardless of the cause of the change, the salivary putrefaction rate as measured by the rate of volatile production may be an indication of a patient's oral health.

One of the volatile sulfur compounds, $H_2S$, is highly toxic to the epithelial tissues of the throat and eyes (Grant, WHM, "Toxicology of the Eye", Charles Thomas, Publisher, 1962). This compound, which is increased in inflamed periodontal pockets, can be detected via its interaction with metal ions, such as barium or mercury (Rizzo, Periodentics 5:233–236, 1967) as well as by the highly sensitive procedures of gas chromatography and mass spectrometry (Tonzetich and Richter, Arch. Oral Biol. 9:39–45, 1964). Furthermore, hydrogen sulfide, as well as the thiols penicillamine and cysteamine, have been shown to solubilize collagen in vitro (Tonzetich and Lo, Arch. Oral Biol. 23:875–880, 1976). Thus it is conceivable that this common product of bacterial metabolism may contribute to the etiology of periodontal disease. Certain low molecular weight nitrogen-containing compounds, such as ammonia and urea (Golub et al, J. Periodontal Res. 6:243–251, 1971), which are found in gingival crevicular fluid, have also been implicated as possible etiologic factors in periodontal diseases.

In view of the above, it may be seen that the causes and influences and aggravating factors effecting periodontal disease are complex, thereby heightening the desirability of developing early detection and treatment methods.

SUMMARY OF THE INVENTION

The present invention relates generally to a novel method of diagnosing periodontal disease, particularly in its early stages. Using sensitive analytical techniques, it has been found that people suffering from this disease produce pyridine and alkyl-pyridine compounds in their oral cavity, whereas people who do not suffer from this disease (i.e., those with healthy oral cavities), produce little or none of these compounds. In accordance with the preferred embodiment of the present invention, an appropriate indicator means for sensing the concentration of pyridines or alkyl-pyridines is provided to test one or more of the following test substances:

1. Mouth air;
2. Saliva;
3. The headspace about incubated saliva; and
4. Air in the gingival crevice.

The preferred indicator means of the present invention is a gas chromatograph and/or a gas chromatograph-mass spectrometer. In order to aid in the evaluation of the above-mentioned test substances, the gas chromatograph may preferably be fitted with a nitrogen specific detector which will aid in identifying nitrogen containing compounds, thereby more easily enabling the operator of the chromatograph to identify whether or not the above-mentioned pyridines or alkyl-pyridines are in fact present in the test substances.

Since the above-identified nitrogen containing aromatic compounds are specifically related to the disease process, monitoring the presence and abundance of these compounds serves the following diagnostic functions:

(A). whether degradative changes are occurring;
(B). how far these changes have advanced; and
(C). how treatment of the disease is progressing. As a result, a significant diagnostic tool is provided by the method of the present invention which should advance early detection and treatment of periodontal disease.

In an alternate embodiment of the present invention, the above-identified test substances are evaluated to determine whether elevated levels of other compounds exist which may indicate or confirm a diagnosis of periodontal disease. In the preferred embodiment, these substances comprise dodecanol, tetradecanol, hexadecanol, dimethyldisulfide, dimethyltrisulfide, phenol, and p-Cresol. The preferred embodiment pyridines to be detected are pyridine, 2-methylpyridine, 3-methylpyridine, and 4-methylpyridine. Accordingly, diagnosis may be made through an indicator means which responds to at least one compound whose presence in the test substance is indicative of periodontal disease.

DETAILED DESCRIPTION OF THE INVENTION

Although specific forms of the invention have been selected for illustration in the drawings, and the following description is drawn in specific terms for the purpose of describing these forms of the invention, this description is not intended to limit the scope of the invention which is defined in the appended claims.

The method of the present invention has been experimentally confirmed using gas chromatography (GC) and gas chromatography-mass spectrometry (GC/MS) which have been employed in this context to analyze the constituents of whole saliva. These techniques have allowed the examination of a large number of constituents, previously unexamined, in relation to the oral health of human subjects. These tests have been conducted as described hereinbelow:

Four male and three female volunteers displaying healthy oral cavities were recruited from employees of the Monell Chemical Senses Center, Philadelphia, Pa. Saliva samples from these subjects were collected in the morning before the subjects had eaten, drank, smoked or engaged in any oral hygiene procedures. Four males and three females having moderate to severe periodontitis were drawn from the patient population of the School of Dental Medicine, University of Pennsylvania and the Veterans Administration Hospital, Philadelphia, Pa. Each of these subjects was instructed to abstain from oral hygiene and ingestion of food or liquid for at least 3 hours prior to collection of saliva samples (Tonzetich, J. and Ng, S.K. 1976. Reduction of Malodor By Oral Cleaning Procedures. Oral Surg., Oral Med., Oral Path., 42: 172-181). All subjects were in good general health and were given a thorough oral examination to determine the health status of their oral cavity. Subjects with rampant caries or with soft tissue lesions not directly related to their periodontal disease were excluded from this study.

The periodontal examination consisted of the following indices:

1. The gingival index (Loe. H. and Silness, J. 1963. Periodontal Disease In Pregnancy. I. Prevalance and Severity. Acta Odont. Scand. 21: 533:549);
2. The plaque index (Sillness, J. and Loe, H. 1964. Periodontal Disease In Pregnancy. II Correlation Between Oral Hygiene and Periodontal Condition. Acta Ondt. Scand. 22: 121-135);
3. The periodontal disease index (Ramfjord, S.P. 1959. Indices for Prevalence and Incidence of Periodontal Disease. J. Perio. 30: 51-59); and
4. The Periodontal index (Russell, A.L. 1956. A System Of Classification and Scoring For Prevalence Surveys of Periodontal Disease. J. Dent. Res. 35: 350-359).

The gingival, plaque and periodontal disease indices were done only on teeth #3, 9, 12, 19, 25, and 28 (Jamison, H. 1960. Prevalence and Severity of Periodontal Disease on a Sample Population. Thesis. University of Michigan, School of Public Health, Ann Arbor). The periodontal index was performed on all teeth with the exception of 3rd molars. In addition to the clinical examination, radiographs were used in determining the periodontal index score. Thus, a score of 4 was possible for individual teeth (radiographic evidence of incipient bone loss). This modification was described by Russell, A.L. 1956. A System of Classification And Scoring For Prevalence Surveys of Periodontal Disease. J. Dent. Res. 335: 350-359.

In examination of the headspace above saliva, each subject donated 10 ml of gum based (polyvinyl acetate) stimulated saliva within a 10 minute interval. Five ml of the sample were placed into a precleaned 25 ml, 2-neck, round bottom flask and sealed with Teflon ™ joints through which a nitrogen line and collection tube passed. Diethylphthalate (523 ug) was employed as the internal standard and added to each saliva sample before beginning the incubation. The saliva was then incubated at 37° C. for 90 minutes under a nitrogen flow of 120 ml/min. Saliva headspace volatiles were swept by the nitrogen stream into a stainless steel collection tube (150 mm × 1.5 mm) filled with Tenax (Applied Science Laboratory, State College, Pennsylvania) which is a porous organic polymer which absorbs organic constituents with little or no retention of water. The remaining 5 ml of saliva were frozen at −60° C. until needed for duplicate analyses.

Gas chromatography (GC) and gas chromatography/mass spec. (GC/MS) were used to study the mixture of volatile organic compounds in the headspace above incubated saliva. Both GC and GC/MS are highly sensitive techniques and are suitable methods of choice for analysis of complex mixtures.

Organic materials collected on the Tenax traps were desorbed from the polymer by rapidly heating the tube to 240° C. for 15 minutes. The volatile organics were swept and condensed onto the front 15 cm of a chromatographic column which was cooled with dry ice. Following this, the dry ice was removed from the column, the Tenax tube was removed from the injection port, the carrier flow was resumed through the column and the chromatograph's oven brought to its starting temperature of 70° C. Components were separated on a 10′, 10% Carbowax 20 M column using temperature programming and the following conditions: injection port 260° C.; flame ionization detector 260°; and a column carrier gas flow of 40 ml/min of helium. The temperature program employed in all GC and GC/MS runs was 70° for 4 minutes, 70° to 230° at 4°/min and then the final temperature of 230° was held for 16 min.

Relative GC retention items of unknowns and authentic standards were obtained by comparing their elution time with a series of $C_2$-$C_{18}$ fatty acid ethyl esters. This yields an "ethyl ester index" (Van denDool, H. and Kratz, P.D. 1963. A Generalization of the Retention Index System Including Linear Temperature Programmed Gas-Lipid Partition Chromatography. J. Chromatog. 11: 463:471) for each compound being studied.

The GS/MS system consisted of a Perkin-Elmer 990 GC interfaced to a Hitachi/Perkin Elmer RMU-6L mass spectrometer via a Watson-Biemann separator (Watson, J. T. and Biemann, K. 1965. Direct Recording of High Resolution Mass Spectra of Gas Chromatographic Effluents. Anal. Chem. 37: 844-851). The separator was kept at 270° C. and the ionization chamber at 175° C. Ionization voltage was 70 eV. Mass spectra were scanned from m/z 12 to 400 in 6 seconds. Identification of all compounds was confirmed by comparison of mass spectra and GC retention times with those authentic samples, literature spectra and/or mass spectra from computer library compilations.

The volatile organic constituents in headspace above incubated saliva were analyzed by GC and GC/MS from all subjects. One half of the subjects (n=7) were considered to have essentially normal, healthy mouths. The 7 remaining subjects were rated as having moderate to severe periodontitis. Four subjects representative of this population and their corresponding oral health indices may be seen in Table 1.

TABLE 1

| | Oral Health Indices | | | |
|---|---|---|---|---|
| | Subject Number | | | |
| Indices | 1* | 2+ | 3+ | 4* |
| Periodontal Index (PI) | 0.46 | 0.54 | 4.0 | 6.2 |
| Periodontal Disease Index (PDI) | 0.50 | 0.54 | 4.6 | 3.4 |
| Plaque Index (PLI) | 0.04 | 0.25 | 2.3 | 1.6 |
| Gingival Index (GI) | 0.13 | 0.42 | 2.0 | 1.5 |

*Indicates female subject
+Indicates male subject

Figure 1:
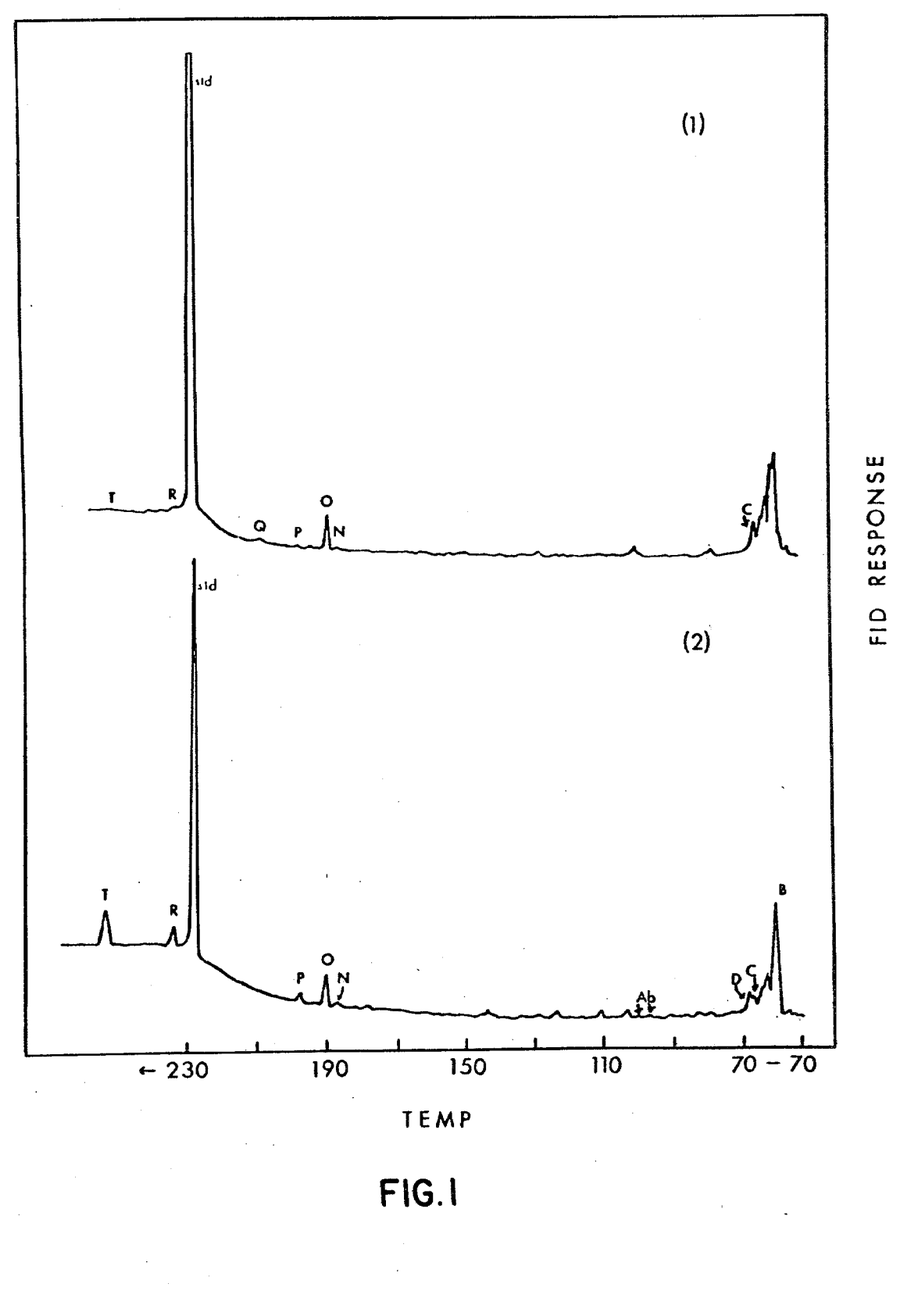
FIG. 1 are gas chromatograms of the headspace above incubated whole saliva of two subjects with good oral health, labeled (1) and (2), respectively.
Figure 2:
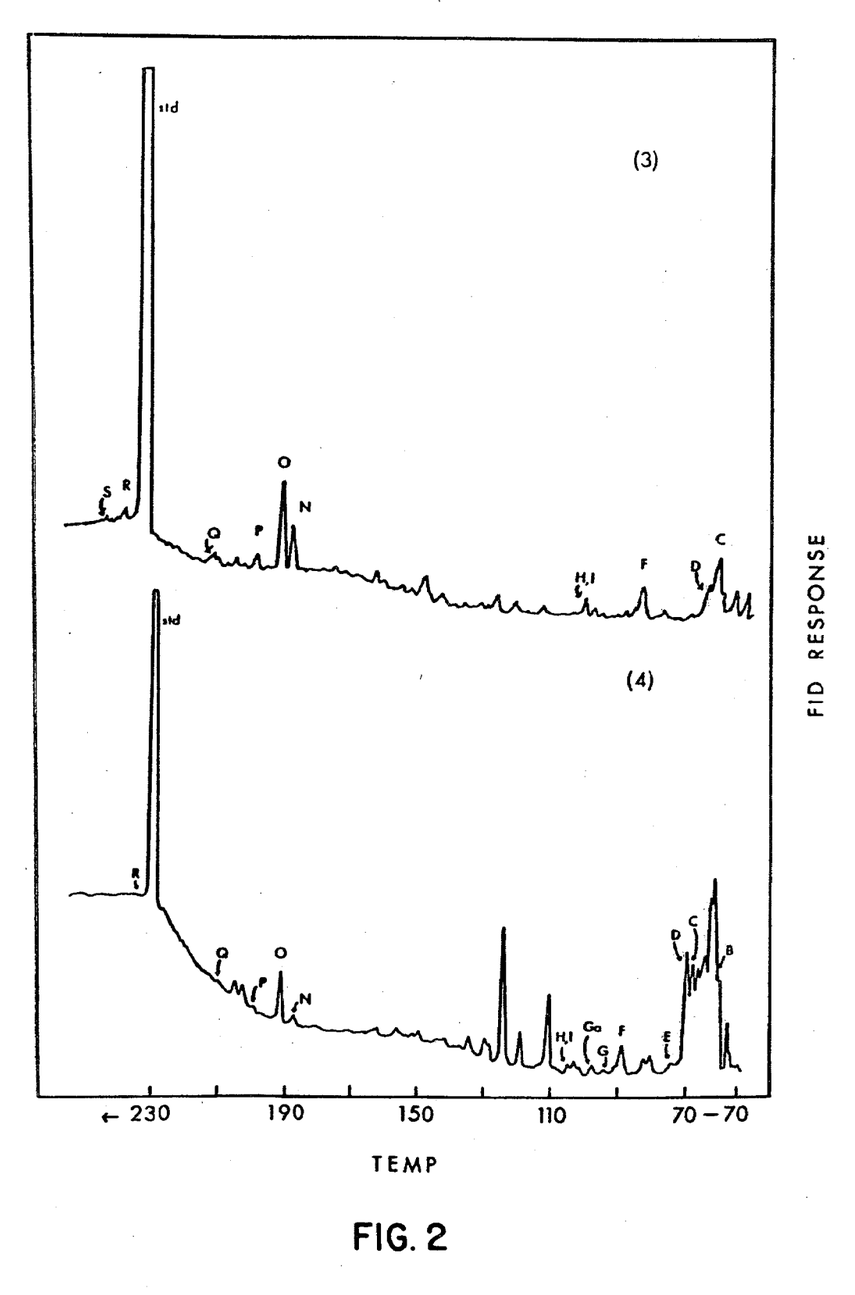
FIG. 2 are gas chromatograms of the headspace above the incubated whole saliva of two subjects with moderate to severe periodontitis, labeled (3) and (4), respectively.

As may be seen from FIG. 1 the normal subjects, with low values for each of the indices, show relatively simple chromatographic profiles indicating only small amounts of volatiles were collected from their incubated saliva in 90 minutes. In contrast as seen from FIG. 2, more complex chromatographic profiles of volatiles were obtained for subjects #3 and #4. These differ both quantitatively and qualitatively from the normals. The identity of the compounds labeled by letters (FIG. 1) are listed in Table 2.

Of particular interest was the identification of pyridine and its 2-, 3- and 4-methyl analogues which were obtained only from subjects with moderate to severe periodontitis. These compounds were absent in subjects with good oral health at the routine sensitivity of the employed GC/MS system. This operating sensitivity is such that 10 ng of either pyridine of one of its methyl derivatives (i.e. 2-, 3-, or 4-) injected into the GC/MS produces a recognizable mass spectrum.

Figure 3:
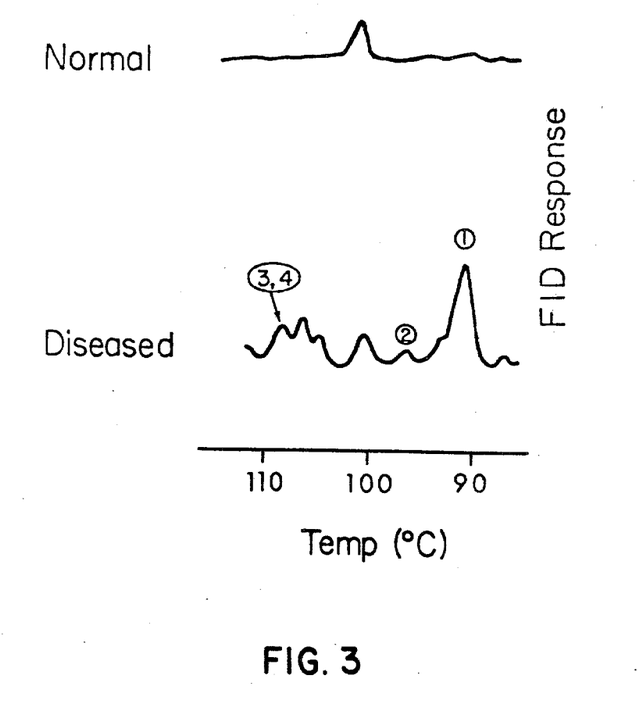
FIG. 3 is an enlarged gas chromatographic trace of the area in which pyridine (1) and 2-, 3-, 4- methyl pyridine (2–4 respectively) elute for a subject with good oral health and a subject with periodontitis.

FIG. 3 shows the portion of the chromatographic profile where pyridine and the methyl pyridines elute. It is clearly shown, that the upper chromatographic trace from the healthy subject (3L, Table 1) is relatively flat while the corresponding trace from the diseased subjects (#4, Table 1) contains several constituents with the pyridines clearly indicated. The amounts seen are in the range of $\leq 0.1$ μg–0.3 μg which is well above the limit required for compound identification.

Table 2 lists a number of compounds which are not found in FIG. 1 but have been identified in the headspace above incubated saliva from 1 or more of the 14 subjects. The majority of compounds isolated and identified from both healthy and diseased subjects appear to be aliphatic and aromatic alcohols. In addition, sulfur compounds (e.g. dimethyl di- and trisulfides) and heterocyclic aromatics (e.g. indole) have been consistently observed in these samples. Although alkyl and aromatic hydrocarbons have been identified, they are not found in samples from all subjects, suggesting that they may not be related to the subject's oral health status.

TABLE 2

| COMPOUNDS FOUND IN THE SALIVARY HEADSPACE OF SUBJECTS WITH DIFFERENT ORAL HEALTH | | | | |
|---|---|---|---|---|
| | Identified By: | | Found in all Subjects ≠ | Elevated in Subjects ≠ with |
| Compounds (Peak ID-FIG. 1) | Mass Spectrum | G.C. Ret. Time | (Normal Subjects N = 7) | Periodontal Disease (N = 7) |
| Ethyl Alcohol (B) | yes*** | — | yes | |
| Propanol (D) | yes*** | yes | yes | |
| Decanol | yes*** | yes | yes | |
| Dodecanol (N) | yes*** | yes | yes | yes |
| Tetradecanol (Q) | yes*** | yes | yes | yes |
| Hexadecanol | yes*** | yes | yes | yes |
| 2-Ethylhexanol | yes** | — | yes | |
| Dimethyldisulfide (E) | yes*** | yes | yes | yes |
| Dimethyltrisulfide (K) | yes*** | yes | ? | yes |
| Benzylalcohol (L) | yes*** | yes | yes | |
| Phenylethanol (M) | yes*** | yes | yes | |
| Phenol (O) | yes*** | yes | yes | yes |
| p-Cresol (P) | yes*** | yes | yes | yes |
| Pyridine (F) | yes*** | yes | — | yes |
| 2-Methylpyridine (G) | yes*** | yes | — | yes |
| 3-Methylpyridine (H) | yes*** | yes | — | yes |
| 4-Methylpyridine (I) | yes*** | yes | — | yes |
| Indole (R) | yes*** | yes | yes | |
| Skatole (S) | yes** | yes | yes | |
| Diphenylamine (T) | yes*** | yes | yes | |
| Benzaldehyde (J) | yes*** | yes | ≠≠ | |
| C8-C12 alkanes (6) | yes** | | ≠≠ | |
| C17 alkane | yes** | | ≠≠ | |
| Tetrachloroethylene (C) ≠≠≠ | yes** | yes | yes | |
| Dimethylfuran (A) | yes** | — | ≠≠ | |
| Acetone | yes** | yes | ≠≠ | |
| Benzene | yes*** | yes | ≠≠ | |
| Toluene | yes*** | yes | ≠≠ | |
| C2-C4 alkyl benzenes (Ab) | yes* | | ≠≠ | |
| Styrene (Ga) | yes** | yes | ≠≠ | |

*Interpreted by Mass Spectrum;
**Comparison with literature M.S.
***Comparison with literature and authentic sample M.S.
≠ Typical Oral Health Indices for normal and diseased subjects may be seen in Table 1.
≠≠ Not found in all subjects, but does not appear to be related to oral health status.
≠≠≠ Tetrachloroethylene is an environmental pollutant, identified by the EPA, as well as in our laboratories, as a constituent of Philadelphia drinking water.

Several compounds which were identified in both healthy and diseased subjects, were elevated in diseased subjects, and are indicated in Table 2. The aliphatic alcohols dodecanol and tetradecanol as well as the aromatic alcohols phenol and p-cresol were found in larger concentration in all subjects with periodontitis. Dimethyl disulfide and dimethyl trisulfide were elevated in saliva from diseased oral cavities compared to saliva from normal subjects. Furthermore, the trisulfide was not always detected in the normal subjects.

The present invention serves to unite two distinct disciplines, dentistry and analytical organic chemistry, to elucidate diagnostic and/or etiologic factors which may participate in the progression of periodontitis.

The above described results clearly indicate that pyridine and one or more methyl pyridines are present in the headspace above saliva from patients suffering from moderate to severe periodontitis. Because the headspace from incubated saliva contains essentially the same volatiles, albeit in greater concentration (Tonzetich, J. 1971. Direct Gas Chromatographic Analysis of Sulphur Compounds in Mouth Air in Man. Archs. Oral Biol. 16: 587–597. and Tonzetich, J. 1977. Production and Origin of Oral Malodor. J. Periodont. 48: 13–20) as mouth air, direct examination of mouth air, direct examination of mouth air from patients suffering from periodontitis will show these pyridine compounds, as will sampling of air from the gingival crevice and/or sampling saliva itself.

Other investigators have suggested that a correlation exists between increased amounts of the volatile sulfur compounds (VSC) $H_2S$, $CH_3SH$, and $(CH_3)_2S$ and increased values of the 4 oral health indices (Rao, G. S., McLennon, D.A., Hefferren, J. J., Appelgren, R. and Robinson, P. J. 1978, Gas Chromatographic Analysis of Mouth Odor as a Potential Diagnostic Aid in Periodontal Disease. J. Dent. Res. 57(A): 244; Tonzetich, 1979). The VSC have been demonstrated in mouths of all persons but are significantly increased in persons with periodontal involvement (Tonzetich, J., 1977, Production and Origin of Oral Malodor. J. Periodont. 48: 13–20. In addition, a recent study (Tonzetich, J. 1978. Oral Malodour: An Indicator of Health Status and Oral Cleanliness. Int. Dent. J. 28: 309–319), indicates that the VSC show cyclic variations in concentration in female patients, increasing 2 to 4-fold during midcycle and menstruation. Using existing techniques, this could complicate the early diagnosis of periodontal involvement in female patients. In accordance with the present invention, however, the pyridines in the headspace above incubated saliva are found only in men and women with periodontitis. Thus, these compounds are particularly reliable indicators of early degradative changes, particularly in women of reproductive age.

The occurrence of pyridine and the pinolines in the salivary volatiles of diseased subjects suggests that they are related to the disease process. Both the 2- and 3-methyl pyridines bear structural similarity to nicotinic and picolinic acids, respectively, and could be produced by biological reduction of these compounds which could also yield pyridine. However, their exact origin is not presently known.

By cataloging many of the volatile substances above incubated saliva in normal and diseased subjects, alternative methods are provided which have diagnostic potential for periodontitis. The analytical techniques applied to the analysis of the headspace allows the monitoring of an array of organic compounds of varied structural type at the parts per million to the parts per billion levels. This is possible because the preferred indicator means relies upon the high sensitivity and resolving power of the gas chromatograph in conjunction with the mass spectrometer's inherent ability to yield a large amount of structural information from a microgram or less of organic compounds. It is within the scope of the present invention to use alternate indicator means which will respond to the presence of one or more of the above—identified compounds in a given test substance. For example, it is within the scope of the present invention to provide a substantially inert binder which is impregnated with a colorimetrically active chemical indicator which may qualitatively respond to the presence of one or more of the above-identified compounds to provide a quick, simple and inexpensive indication that the patient from whom the test substance has been derived has periodontal disease.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. A method of evaluating an individual to determine and diagnose the existence of periodontal disease in the oral cavity of that individual, comprising the steps of:
   (a) collecting a test substance from the oral cavity of the individual to be evaluated; and
   (b) presenting that test substance to an indicator means for selectively responding at least qualitatively to the presence of at least one indicative diagnostic pyridine compound in that test substance, whereby a qualitative response of said indicator means diagnoses the existence of periodontal disease in said individual.

2. The method of claim 1 wherein step (a) comprises collecting saliva from that individual.

3. The method of claim 2 wherein step (a) comprises the steps of incubating said saliva and collecting air from the headspace adjacent said saliva.

4. The method of claim 1 wherein step (a) comprises collecting air from at least one gingival crevice of said individual.

5. The method of claim 1 wherein step (a) comprises collecting mouth air from said individual.

6. The method of claim 1 wherein step (b) comprises providing an indicator means for qualitatively responding to at least pyridine.

7. The method of claim 1 wherein step (b) comprises providing an indicator means for qualitatively responding to at least a picoline.

8. The method of claim 1 wherein step (b) comprises providing an indicator means for qualitatively responding to at least 2-methyl pyridine.

9. The method of claim 1 wherein step (b) comprises providing an indicator means for qualitatively responding to at least 3-methyl pyridine.

10. The method of claim 1 wherein said indicator means also responds quantitatively to at least a second indicative diagnostic compound to sense and indicate increased concentrations thereof, said increased concentrations being indicative of the existence of periodontal disease in said individual.

11. The method of claim 10 wherein said indicator means responds quantitatively to sense and indicate concentrations of p-cresol.

12. The method of claim 10 wherein said indicator means responds quantitatively to sense and indicate increased concentrations of phenol.

13. The method of claim 10 wherein said indicator means responds quantitatively to sense and indicate increased concentrations of dimethyltrisulfide.

14. The method of claim 10 wherein said indicator means responds quantitatively to sense and indicate increased concentrations of dimethyldisulfide.

15. The method of claim 10 wherein said indicator means responds quantitatively to sense and indicate increased concentrations of hexadecanol.

16. The method of claim 10 wherein said indicator means responds quantitatively to sense and indicate increased concentrations of tetradecanol.

17. The method of claim 10 wherein said indicator means responds quantitatively to sense and indicate increased concentrations of dodecanol.

* * * * *